(12) United States Patent
Toyoda et al.

(10) Patent No.: US 7,931,862 B2
(45) Date of Patent: Apr. 26, 2011

(54) SAMPLE RACK TRANSFER APPARATUS

(75) Inventors: Akio Toyoda, Kobe (JP); Hiroki Koike, Kobe (JP); Yoichi Nakamura, Kobe (JP)

(73) Assignee: Sysmex Corporation, Hyogo (JP)

( * ) Notice: Subject to any disclaimer, the term of this patent is extended or adjusted under 35 U.S.C. 154(b) by 814 days.

(21) Appl. No.: 11/344,393

(22) Filed: Jan. 31, 2006

(65) Prior Publication Data
US 2006/0193754 A1 Aug. 31, 2006

(30) Foreign Application Priority Data

Jan. 31, 2005 (JP) .................................. 2005-023133

(51) Int. Cl.
*G01N 21/13* (2006.01)
(52) U.S. Cl. ............ 422/65; 422/63; 422/68.1; 422/62; 422/67; 422/104
(58) Field of Classification Search .................... 422/58, 422/62–67, 104
See application file for complete search history.

(56) References Cited

U.S. PATENT DOCUMENTS

| | | | |
|---|---|---|---|
| 5,679,059 A | | 10/1997 | Nishi et al. |
| 5,772,963 A | * | 6/1998 | Cantatore et al. ............... 422/67 |
| 5,972,295 A | * | 10/1999 | Hanawa et al. ................. 422/65 |
| 6,079,707 A | * | 6/2000 | Fujiwara et al. ............... 271/207 |
| 6,290,907 B1 | * | 9/2001 | Takahashi et al. .............. 422/65 |
| 6,522,976 B2 | | 2/2003 | Shiba et al. |
| 6,764,649 B2 | * | 7/2004 | Ammann ........................ 422/63 |
| 2004/0147012 A1 | * | 7/2004 | Yokoi et al. ................ 435/287.3 |

FOREIGN PATENT DOCUMENTS

| | | |
|---|---|---|
| JP | 08-187658 A | 7/1996 |
| JP | H09-243645 A | 9/1997 |
| JP | 2001-112122 A | 4/2001 |
| JP | 2002-048802 A | 2/2002 |

* cited by examiner

*Primary Examiner* — Jill Warden
*Assistant Examiner* — Dean Kwak
(74) *Attorney, Agent, or Firm* — Brinks Hofer Gilson & Lione

(57) ABSTRACT

A sample rack transport apparatus for transporting a sample rack holding a container containing a sample is provided with a rack transport mechanism for transporting sample racks, and a control unit for controlling the operation of the transport mechanism. The transport mechanism has actuators, and the samples rack is transported by the operation of these actuators. The control unit is accommodated in a control box. The transport mechanism and control box are supported in a case. The control box is provided below the transport mechanism, and is configured so as to be slidably transferred into and from the case.

17 Claims, 8 Drawing Sheets

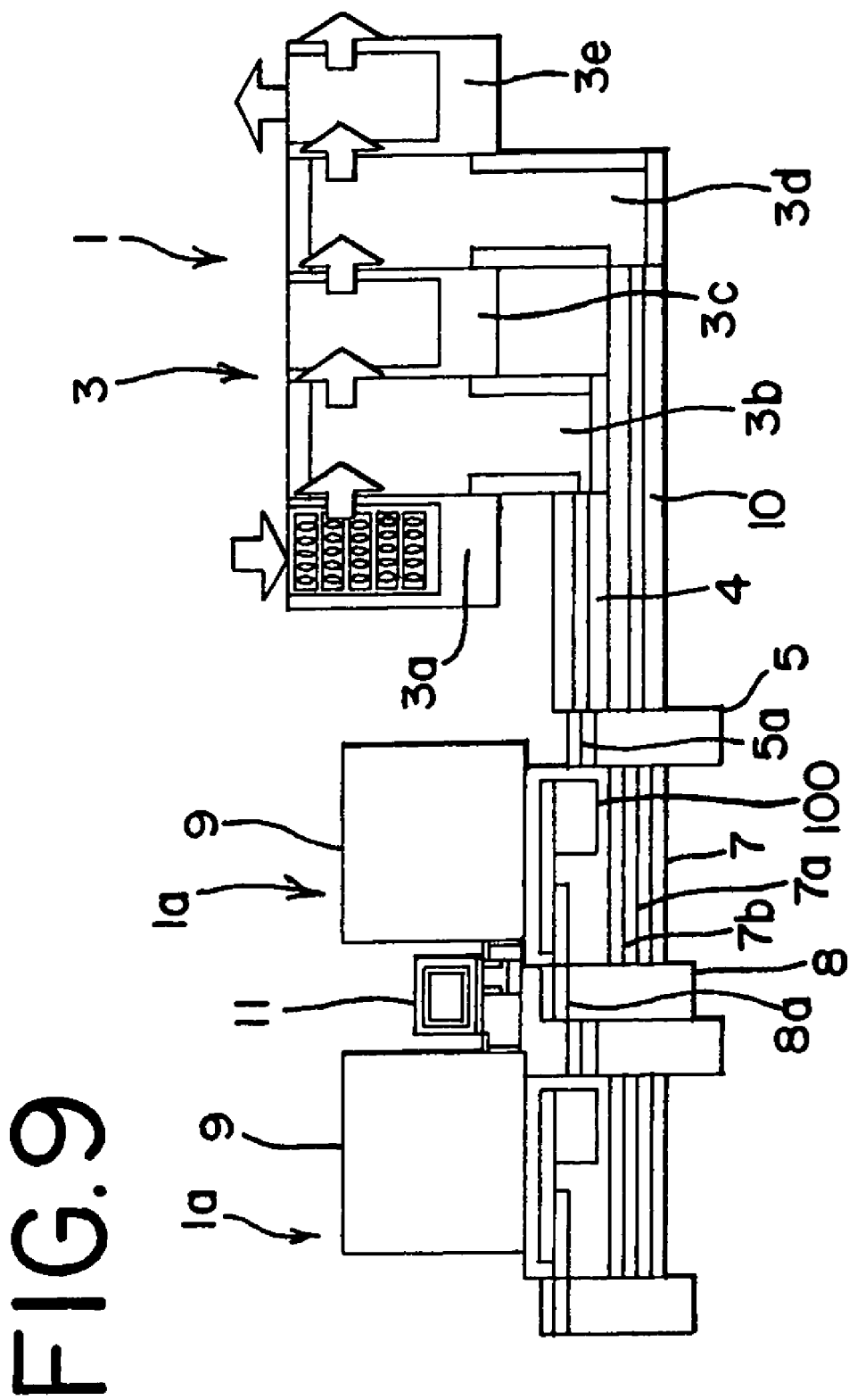

SAMPLE RACK TRANSFER APPARATUS

This application claims priority under 35 U.S.C. §119 to Japanese Patent Application No. 2005-023133 filed Jan. 31, 2005, the entire content of which is hereby incorporated herein by reference.

FIELD OF THE INVENTION

The present invention relates to a sample rack transport apparatus for transporting a sample rack holding containers containing samples.

BACKGROUND

In recent years there has been an increase in the number of sample processes and number of analysis items in blood testings and urine testings performed in clinical laboratories, such as are found in hospitals and testing centers, which has lead to demand for greater efficiency. Therefore, in order to efficiently perform a large quantity of sample testings, sample rack transport apparatuses for sequentially transporting sample racks have come to be used in analyzers such as hemocyte analyzers and urine analyzers to transport sample racks that hold sample containers containing samples, such as blood and urine (for example, refer to Japanese Laid-Open Patent Publication No. 9-243645).

The sample rack transport apparatus disclosed in Japanese Laid-Open Patent Publication No. 9-243645 is provided with a control unit for controlling the operation of the transport mechanism and a case for supporting the transport mechanism that transports the samples racks, and the control unit is provided within the case.

In routine maintenances of the sample rack transport apparatus, it is necessary to expose the control unit of the sample rack transport apparatus after the shutdown. However, in the sample rack transport apparatus disclosed in Japanese Laid-Open Patent Publication No. 9-243645, it is necessary to remove side plates and the transport mechanism from the apparatus to expose the control unit. And it takes extra time and effort to perform the routine maintenances.

SUMMARY

The scope of the present invention is defined solely by the appended claims, and is not affected to any degree by the statements within this summary.

A first aspect of the present invention is a sample rack transport apparatus for transporting a sample rack holding containers containing samples, comprising a transport mechanism for transporting a sample rack; a control unit for controlling the operation of the transport mechanism; a control box for housing the control unit; and a case for holding the transport mechanism and control box; wherein the control box is structured so as to be able to be inserted into the case and drawn from the case.

A second aspect of the present invention is a sample rack transport apparatus for transporting a sample rack holding containers containing samples, comprising a transport mechanism for transporting a sample rack; a control unit for controlling the operation of the transport mechanism; a control box for housing the control unit; and a case for holding the transport mechanism and control box; wherein the control box is structured so as to be slidably transferred into and from the case.

BRIEF DESCRIPTION OF THE DRAWINGS

FIG. 9 is a schematic view showing the structure of the system during normal use of the sample rack transport apparatus of an embodiment of the present invention.

DETAILED DESCRIPTION OF THE PREFERRED EMBODIMENTS

The preferred embodiments of the present invention are described hereinafter with reference to the drawings.

Figure 1:
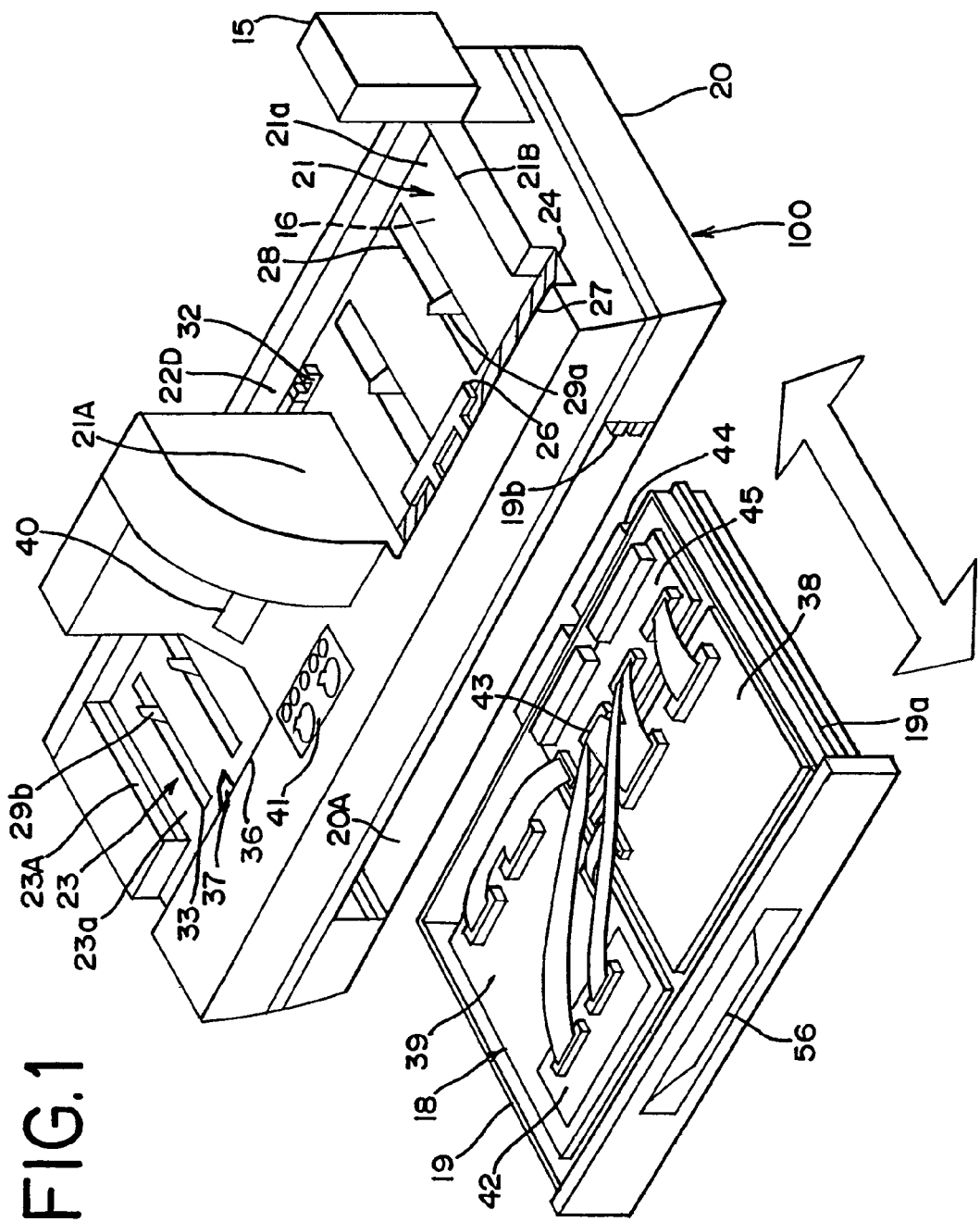
FIG. 1 is an external perspective view of the structure of the sample rack transport apparatus of an embodiment of the present invention.
Figure 2:
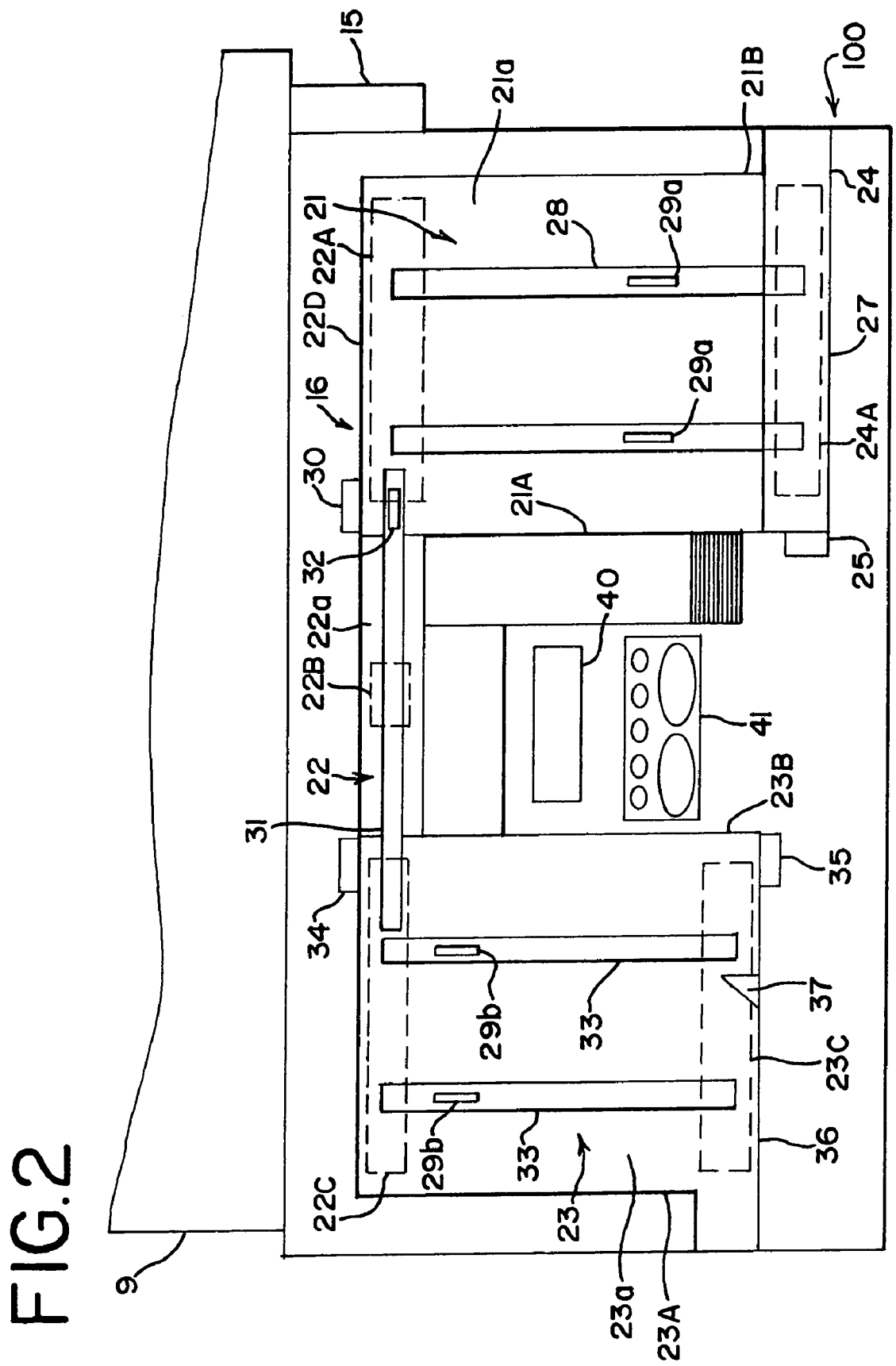
FIG. 2 is plan view of the structure of the top part of the sample rack transport apparatus of an embodiment of the present invention.

FIG. 1 is an external perspective view of the overall structure of the sample rack transport apparatus 100 of an embodiment of the present invention, and FIG. 2 is a plan view showing the structure of the top part of the sample rack transport apparatus 100. As shown in FIG. 1, the sample rack transport apparatus 100 is mainly configured by a transport mechanism 16 for transporting sample racks, control box 19 for installing a control unit 18 for controlling the operation and the like of the transport mechanism 16, and a case 20 for supporting same. As shown in FIG. 2, the sample rack transport apparatus 100 is connected to a blood analyzer 9, and is structured so as to supply blood samples to the blood analyzer 9. The blood samples are accommodated in sample containers, which are described below, and a plurality of samples containers are held in a sample rack described later. The sample rack is transported by the sample rack transport apparatus 100.

Figure 3:
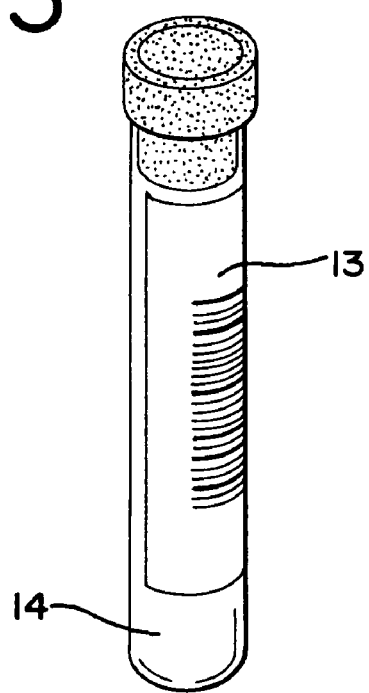
FIG. 3 is a perspective view showing the external appearance of a sample container used in the sample rack transport apparatus of an embodiment of the present invention.
Figure 4:
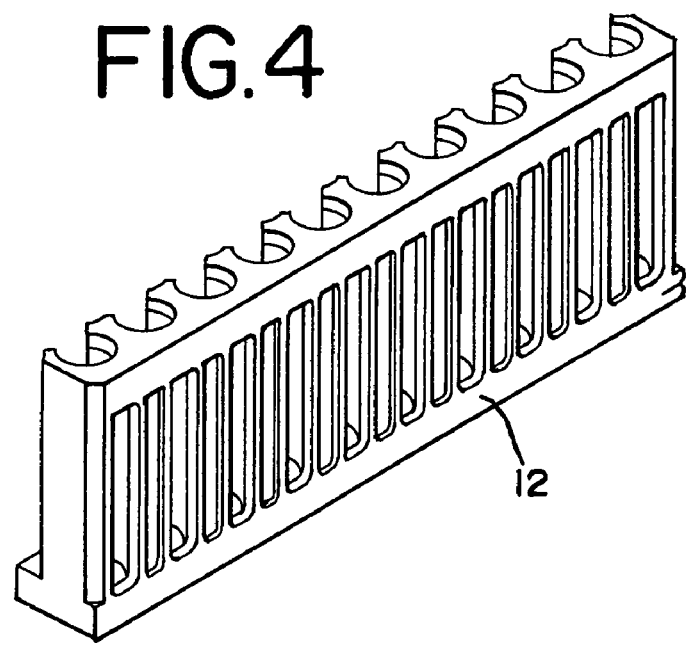
FIG. 4 is a perspective view showing the external appearance of a sample rack used in the sample rack transport apparatus of an embodiment of the present invention.

FIG. 3 is a perspective view showing the exterior of a sample container for accommodating a blood sample, and FIG. 4 is a perspective view showing the exterior of the sample rack for holding the sample container. As shown in FIG. 4, a sample container 14 has a narrow tube-like shape with a closed, rounded bottom at one end so as to be capable of holding a blood sample; on the side of the container is adhered a barcode label on which is printed a barcode indicating information such as the sample ID number and the like. Furthermore, a sample rack 12 used by the sample rack transport apparatus 100 is shaped so as to be capable of holding a plurality of sample containers 14 in rows, as shown in FIG. 4.

As shown in FIG. 1, the case 20 is formed in an approximate cube shape. A part of the top part is depressed in a concave shape. A start stocker 21 for stocking a plurality of sample racks 12 before analysis, a transport path 22 for transporting the sample racks 12 to a position for delivery to the blood analyzer 9, and an end stocker 23 for stocking the sample racks 12 after analysis are formed therein. A transport mechanism 16 is arranged below the start stocker 21, transport path 22, and end stocker 23.

The transport mechanism 16 has a rack pickup belt 24, T-shaped lever 26, hooks 29a, 29b, 37, and projection 32. The transport mechanism 16 is provided with a plurality of motors, and a conversion mechanism for converting the rotational movement of the motors to linear movement. The conversion mechanism may be configured by, for example, a drive pulley provided on the drive shaft of a motor, a driven pulley, and a timing belt reeved around the pulleys, such that the rotational movement of the motor is converted to linear movement. The pickup belt 24, T-shaped lever 26, hooks 29a, 29b, 37, and projection 32 are driven separately by linkage to the conversion mechanism and motor.

As shown in FIG. 2, the start stocker 21 and end stocker 23 are mutually separated by a predetermined distance (hereinafter, the separation direction is designated the lateral (right-to-left) direction; the direction perpendicular to this direction is designated the front-to-back direction; the direction in which the blood analyzer 9 is arranged relative to the sample rack transport apparatus 100 is designated the [back] direction; the opposite direction is designated the [front] direction; and when facing the [back] direction, the right direction is designated [right] and the left direction is designated [left]). The length direction of the sample rack 12 matches the lateral direction, and is transported through the process facing the top of the sample rack transport apparatus. The start stocker 21 is provided on the right side of the end stocker 23.

The start stocker 21 is provided with a bottom surface 21a, and lateral walls 21A, 21B, 27, and 22D; similarly, the end stocker 23 is provided with a bottom surface 23a, and lateral walls 23A, 23B 36, and 22D. The shape of the bottom surfaces 21a and 23a is a front-to-back rectangular shape, and the width of the of the bottom surfaces 21a and 23a equal with the side-to-side length of the sample rack. The lateral walls 21A and 21B are provided on the right and left ends of the bottom surface 21a, and the lateral wall 27 is provided at the front end, and the lateral wall 22D is provided at the back end. In this way the start stocker 21 is formed in a concave shape one stage lower than the top surface of the case 20. The lateral wall 22D extends to the left from the back end of the start stocker 21, and is a wall used jointly as the back end of the end stocker 23 and transport path 22. Similarly, the lateral walls 23A and 23B are provided at the right and left ends of the bottom surface 23a, the lateral wall 36 is provided at the front end, and the lateral wall 22D is provided at the back end. In this way the end stocker 21 is formed in a concave shape one stage lower than the top surface of the case 20.

The transport path 22 for transporting a sample rack from the start stocker 21 to the end stocker 23 is formed along the lateral wall 22D. The transport path 22, which extends from the bottom surface 21a of the start stocker 21 to the bottom surface 23a of the end stocker 23, is flat so as to smoothly transport the sample rack 12.

The position facing the lateral wall 22D at the back end of the start stocker 21 is the rack horizontal feed start position 22A, and the position facing the lateral wall 27 at the front end of the start stocker 21 is the rack enter position 24A. A rack pickup belt 24 for loading the sample rack 12 in the start stocker is provided at the rack enter position 24A. A sample rack 12 at the rack enter position 24 is taken in from the external supply origin by the rack pickup belt 24. A sensor 25 for detecting the presence of the sample rack is provided at the front end of the lateral wall 21A, and the sensor 25 detects whether or not a sample rack 12 is present at the rack enter position 24A, and outputs a detection signal to the control unit 18. As shown in FIG. 1, A narrow slit (not shown in the drawing) is formed in the lateral direction in the lateral wall 27, and the T-shaped lever 26 is provided so as to extend and retract from the slit. When a sample rack 12 is introduced at the rack enter position 24A, the T-shaped lever 26 is housed within the lateral wall 27 so as to not hinder the entering rack, and when the sample rack 12 is present at the rack enter position 24A, the lever 26 projects backward from the slit and can push the sample rack 12 at the rack enter position 24A. As shown in FIG. 2, two narrow slits 28 are formed in the back direction on the bottom surface 21a, and the hook 29a is provided so as to enter and exit from the two slits 28. The hook 29a is movable forward and back along the slit 28. Accordingly, the hook 29a engages the floor of the sample rack 12, such that the sample rack 12 can be moved to the rack horizontal feed start position 22A by moving the hooks 29a backward in this condition. Furthermore, a sensor 30 for detecting the presence of the sample rack 12 is provided on the lateral wall 22D near the rack horizontal feed start position 24A. The sensor 30 detects whether or not a sample rack 12 is present at the rack horizontal feed start position 24A, and outputs a detection signal to the control unit 18.

The middle part of the transport path 22 is designated sample supply position 22B for supplying a sample container 14 held by the sample rack 12 to the blood analyzer. A slit 31 is formed laterally in the bottom surface 22a, and a projection 32 is provided so as to be capable of entering and exiting from the slit 31. The projection 32 is movable laterally along the slit 31. Accordingly, the projection 32 engages the floor of the sample rack 12, such that the sample rack 12 can be moved to the rack horizontal feed start position 22A described later by moving the projection 32 leftward in this condition.

The position facing the lateral wall 22D at the back end of the end stocker 23 is designated the rack horizontal feed end position 22C, and the position facing the lateral wall 36 at the front end of the end stocker 23 is designated the rack delivery position 23C. A sensor 34 for detecting the presence of a sample rack 12 is provided on the right side at the back end of the end stocker 23. The sensor 34 detects whether or not a sample rack 12 is present at the rack horizontal feed end position 22C, and outputs a detection signal to the control unit 18.

Two narrow slits 33 are formed in the front-to-back direction on the bottom surface 23a, and hooks 29b are provided so as to enter and exit from the two slits 33. The hook 29b is movable forward and back along the slit 33. Accordingly, the hook 29b engages the floor of the sample rack 12, such that the sample rack 12 can be moved to the rack delivery position 23C by moving the hooks 29b forward in this condition. A sensor 35 for detecting the presence of the sample rack 12 is provided at the right end of the lateral wall 36. The sensor 35 detects whether or not the sample rack 12 is present at the rack delivery position 23C, and outputs a detection signal to the control unit 18. A narrow slit (not shown in the drawing) is formed in a lateral direction on the lateral wall 36. A hook 37 is provided so as to project from the slit toward the back. The hook 37 is movable laterally along the slit. In this way the sample rack 12 can be moved from the rack delivery position 23C to a supply destination on the right side by hook 37 pressing against the right side surface of the sample rack 12.

According to this construction, the sample rack 12 is first delivered to the rack enter position 24A by the rack pickup belt 24. When the sample rack 12 has arrived at the rack enter position 24A, the presence of the rack is detected by the sensor 25. Thereafter, the sample racks 12 are pressed backward one rack at a time as the T-shape lever 26 moves backward. A new sample rack 12 arrives at the rack enter position 24A after a sample rack 12 is moved backward. The next sample rack 12 is pressed backward after the previous sample rack 12 has been pressed backward by the T-shape lever 26 pressing the next arrived sample rack 12. The sample racks 12 are stocked in the start stocker 21 by repeating this operation. Then, the hook 29a projects and engages the sample rack 12 stocked in the last position in the start stocker 21, and this sample rack 12 is fed to the rack horizontal feed start position 22A by the backward movement in this condition.

When the sample rack 12 arrives at the rack horizontal feed start position 22A, the presence of the rack is detected by the sensor 30. In this case, the projection 32 protrudes and engages the bottom of the sample rack 12, and moves leftward in this condition. Thus, the sample rack 12 is transported from the rack horizontal feed start position 22A to the rack horizontal feed end position 22C.

When the sample rack 12 arrives at the rack horizontal feed end position 22C, the presence of the rack is detected by the sensor 34. In this case, the hook 29b projects and engages the sample rack 12 stocked at the rack horizontal feed end position 22C, and moves forward in this condition. In this way the sample rack 12 is transported from the rack horizontal feed end position 22C to the rack delivery position 23C. A new sample rack 12 is transported by the projection 32 at the rack horizontal feed end position 22C after the previous sample rack 12 has been moved. This sample rack 12 is transported from the rack horizontal feed end position 22C to the rack delivery position 23C by the hook 29b, and arrives at the back side of the previously transported sample rack 12. The sample racks 12 are stocked in the end stocker 23 by repeating this operation. Furthermore, when the sample rack 12 arrives at the rack delivery position 23C, the sample rack 12 is supplied to a delivery destination at the left side by the movement imparted through the hook 37 pressing against the right side surface of the sample rack 12.

The top surface of the case 20 of the sample rack transport apparatus 100 is provided with a liquid crystal display 40 for displaying the status of the sample rack transport apparatus, and an operation panel 41 which an operator uses to perform the operations of the transport apparatus. The liquid crystal display 40 and operation panel 41 are connected to a user interface control board 42 through a case side interrupt board 46 and a control box side interrupt board 45 described later.

Figure 5:
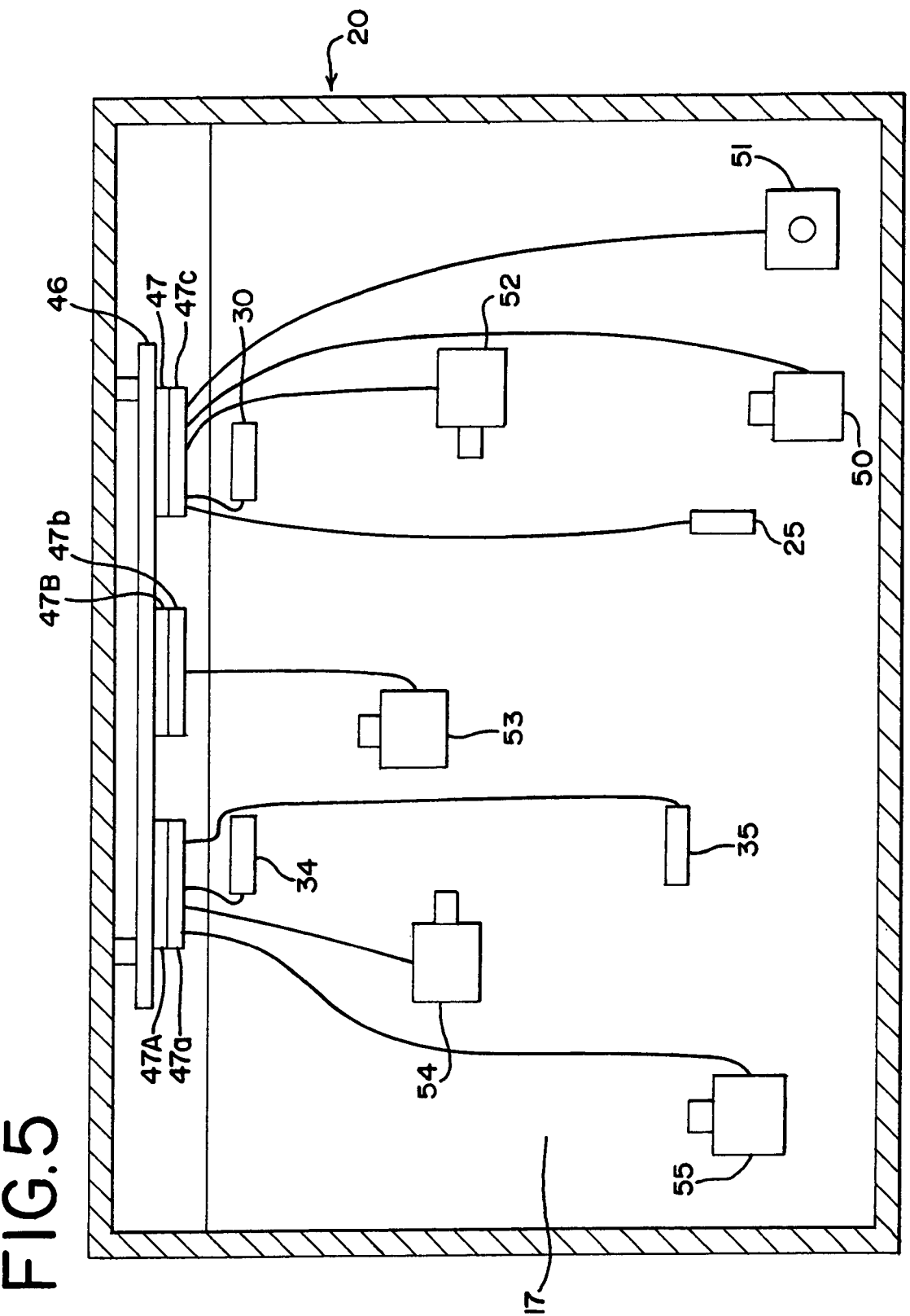
FIG. 5 is a plan view showing the positional relationship of the case side interrupt board described later and the sensors and motors provided in the transport mechanism of the sample rack transport apparatus of an embodiment of the present invention.
Figure 6:
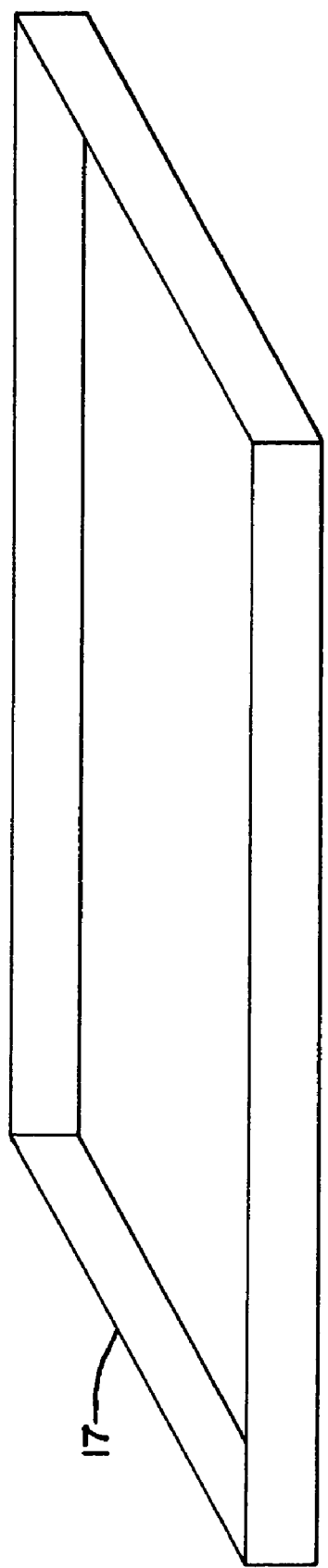
FIG. 6 is a perspective view showing the shape of the intermediate panel of the sample rack transport apparatus of an embodiment of the present invention.

FIG. 5 is a plan view showing the positional relationships of the sensors and motors provided in the transport mechanism 16 of the sample rack transport apparatus 100, and the case side interrupt board 46 described later. As shown in FIG. 5, the transport mechanism 16 is provided with a case side interrupt board 46, motors 50, 51, 52, 53, 54, and 55, sensors 25, 30, 34, and 35. An intermediate panel 17 is provided directly below the transport mechanism 16, such that the transport mechanism 16 is not exposed outside the apparatus. When the control box 19 is accommodated in the case 20, the control unit 18 is positioned directly below the intermediate panel 17, such that the control box 19 is not exposed on the outer side of the intermediate panel 17. FIG. 6 is a perspective view showing the shape of the intermediate panel 17 of the sample rack transport apparatus. As shown in FIG. 6, the edges of the intermediate panel 17 are bent upward, so as to form a concave shape. According to this configuration, when sample is leaked from a sample container 14 during transit of the sample rack 12, the leaked sample is received by the intermediate panel 17, and the sample is prevented from reaching the control unit 18 provided within the control box 19.

As shown in FIG. 1, an aperture 20A is provided on the bottom front surface of the case 20. A hollow space connected to the aperture 20A is formed on the bottom side of the intermediate panel 17, and the control box 19 is accommodated in this space. Guide rails 19b are arranged on both sides of the space of the interior of the case 20. A projection 19a extending front-to-back protrudes on the bilateral side surfaces of the control box 19.

According to this configuration, the control box 19 can be smoothly pulled from the case 20, and the control box 19 can be inserted into the case 20. Furthermore, a handle 56 is provided on the front surface of the control box 19. In this way a user may grip the handle 56 and easily pull the control box 19 from the case 20.

Furthermore, the control box 19 and intermediate panel 17 are magnetic bodies constructed of stainless steel. In this way when the control box 19 is accommodated in the case 20, the perimeter of the control unit 18 is covered by the magnetic material, and since the magnetic material absorbs electromagnetic waves, there is diminished noise radiating from the control unit 18. Therefore, the effects of electromagnetic waves on the work environment are reduced. The intermediate panel 17 may also be configured using materials other than stainless steel, such as carbon steel, permalloy alloy, and other metallic or nonmetallic magnetic materials.

Figure 7:
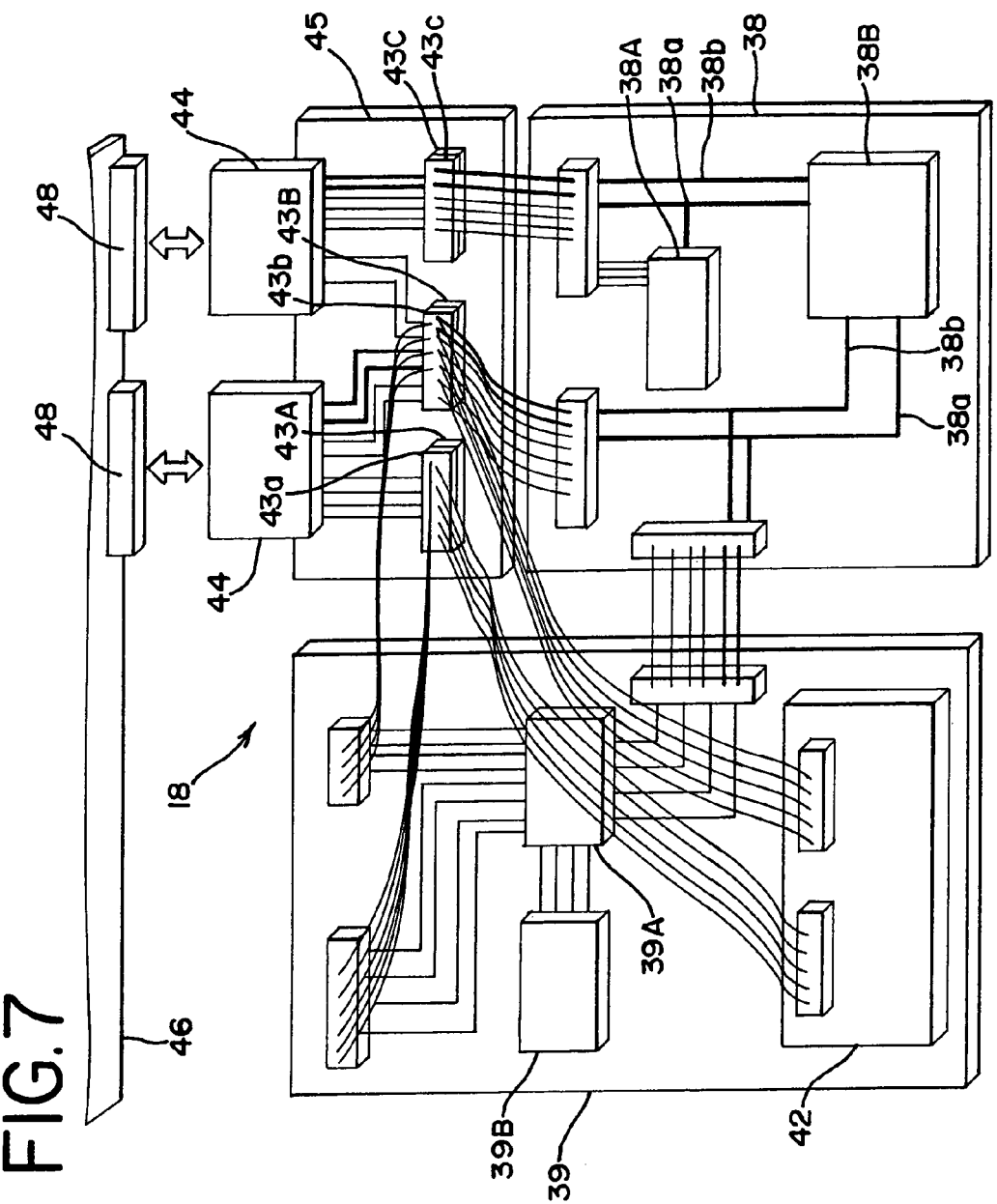
FIG. 7 shows the structure of the control unit of the sample rack transport apparatus of an embodiment of the present invention.

FIG. 7 shows the structure of the control unit 18 of the sample rack transport apparatus 100 and the control box side interrupt board 45 described later. The control unit 18 is accommodated in the control box 19, which is open at the top. As shown in FIG. 7, the control unit 18 is provided with a driver board 38, CPU board 39, user interface control board 42. The driver board 38, CPU board 39, user interface control board 42 are connected to the control box side interrupt board 45 through leads cords so as to be capable of mutually sending and receiving electric signals. The control box side interrupt board 45 is arranged so as to contact the back wall of the control box 19. The driver board 38, CPU board 39, and user interface control board 42 are provided side by side so as to not overlap in the control box 19. The driver board 38 and CPU board 39 are mutually connected through leads cords so as to be capable of mutually sending and receiving electric signals. The user interface control board 42 is provided in front of the CPU board 39. The user interface control board 42 has a bus connected to the CPU board 39, so as to be capable of mutual data transfer with the CPU board 39. The user interface control board 42 is connected to the liquid crystal display 40 and the operation panel 41 through the control box side interrupt board 45 and the case side interrupt board 46.

The driver board 38 has a driver circuit 38A capable of driving a motor, and a power circuit 38B for converting an alternating current of a commercial power source into two types of direction current voltage. The conversion of the alternating current to two types of direct current voltage provides different voltages to drive the sensors and CPU, and to drive the actuators motors. One direct current is supplied to the sensors and CPU, and the other direction current is supplied to the actuators such as motors. The driver board 38 is connected to the motors 50, 51, 52, 53, 54, and 55, and the sensors 25, 30, 34, and 35 through the control box side interrupt board 45 and the case side interrupt board 46. Therefore, the driver board 38 sends detection signals received from the sensors to the CPU board 39, and supplies power to the CPU board 39, sensors, and motors. Furthermore, the driver board 38 drives the motors based on motor control signals received from the CPU board 39.

The CPU board 39 is provided with a CPU 39A and ROM 39B, and computer programs executed by the CPU 39A are stored in the ROM 39B. The CPU board 39 receives the detection signals and output signals from the operation panel 41 through the driver board 38, and the CPU 39A executes the programs stored in the ROM 39B. Furthermore, the CPU board 39A outputs motor control signals for controlling the operation of the actuators such as motors provided in the transport mechanism 16, and display signals for displaying the status of the sample rack transport apparatus 100 to the liquid crystal display 40 based on the detection signals and executed programs.

The user interface control board 42 is capable of displaying the status of the sample rack transport apparatus 100 on the liquid crystal display 40 based on display signals, and sending the output signals of the operation panel 41 to the CPU board 39.

The control box side interrupt board 45 is provided with three control unit connectors 43A, 43B, and 43C, and two control box side connectors 44. The control unit connector 43A engages the control unit side connector 43a, which is connected to leads extending from the CPU board 39 and user interface control board 42; the control unit connector 43B engages the control unit side connector 43b, which is connected by leads extending from the driver board 38, user interface control board 42, and CPU board 39; and the control unit connector 43C engages the control unit side connector 43c, which is connected to leads extending from the driver board 38. Thus, the control box side interrupt board 45 and CPU board 39, driver board 38 and user interface control board 42 are respectively connected.

According to this configuration, the structural elements of the control unit 18, including the driver board 38, CPU board 39, and user interface control board 42, may be exchanged with other driver boards, CPU boards, and user interface boards insofar as such boards satisfy the design specifications of the sample rack transport apparatus 100. Therefore, since it is unnecessary to redesign these boards, the number of development processes and cost of the sample transport apparatus 100 can be reduced.

The lead cords connecting the driver board 38 and control unit connectors 43B, 43C include four power leads 38a for supplying power to the various actuators and sensors. The direct current for driving sensors and the direct current for driving motors are different, and are respectively supplied from power circuits 38B provided on the driver board 38.

The control unit connectors 43A, 43B, 43C and control box side connector 44 are connected through the printed wiring of the control box side interrupt board 45. The control box side connector 44 is provided as two arrangements at the back end of the control box side interrupt board 45, such that the leading end protrudes backward from the aperture provided in the back surface of the control box 19. The control box side connector 44 is connectable to the case side connector 48 provided at the bottom end of the case side interrupt board 46 described later.

Figure 8:
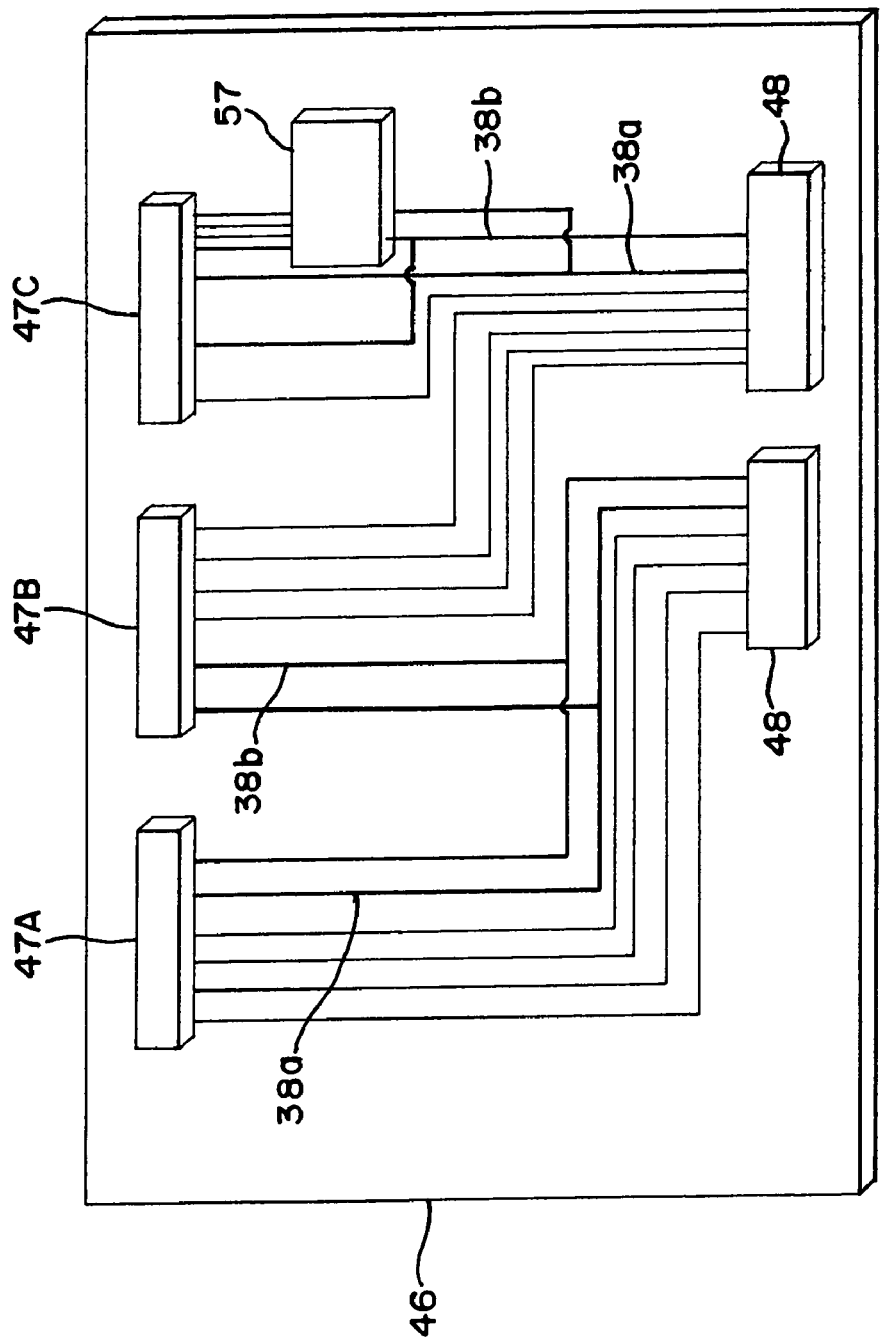
FIG. 8 illustrates the structure of the case side interrupt board provided in the sample rack transport apparatus of an embodiment of the present invention.

FIG. 8 shows the structure of the case side interrupt board 46 provided in the sample rack transport apparatus 100. As shown in FIG. 8, the case side interrupt board 46 is provided with a driver circuit 57 for driving motors, three actuator connectors 47A, 47B, and 47C, and a case side connector 48. As shown in FIG. 5, a gap is formed between the back end of the intermediate panel 17 and the back wall of the case 20. The case side interrupt board 46 is mounted to the back wall of the case 20, and the bottom part extends into the empty space for accommodating the control box 19 provided below the intermediate panel 17, so as to reach a position identical to that of the bottom surface of the control box 19. The actuator connectors 47A, 47B, and 47C are arranged side by side in a lateral direction at the top part of the case side interrupt board 46. The leads that extend to the sensors 34 and 35, and motors 54 and 55 arranged at the left side of the case 20 are connected to the actuator side connector 47a; the leads that extend to the motor 53 disposed in the center of the case 20 are connected to the actuator side connector 47b; and the leads that extend to the sensors 25 and 30, and the motors 50, 51, and 52 disposed at the right side of the case 20 are connected to the actuator side connector 47c. The actuator side connector 47A disposed at the far left side engages the actuator side connector 47a; the actuator connector 47B in the center engages the actuator side connector 47b; and the actuator connector 47C disposed at the far right engages the actuator connector 47c.

According to this configuration, the leads can be shortened from the actuator connectors 47A, 47B, and 47C to each motor and sensor, thus making managing the leads a simple matter.

As shown in FIG. 8, the actuator connectors 47A, 47B, and 47C, and the case side connector 48 are connected through the printed wiring of the case side interrupt board 46. The power leads 38a and ground leads 38b that extend from the case side connector 48 on the printed circuit boards to the actuator connectors 47A, 47B, 47C are branched to several motors and sensors as power receiving objects. For example, when are respectively eight sensors and motors as power receiving objects, the four power leads and corresponding four ground leads 38b extending from the power circuit 38B have eight branches from the case side connector 48 to the actuator connectors 47A, 47B, and 47C, and from the actuator connectors 47A, 47B, and 47C are connected to the sensors and motors. That is, the power leads 38a and ground leads 38b that extend from the power circuit 38B to the control box side connector 44 are fewer than the number of motor and sensors. The power leads 38a and 38b in FIGS. 7 and 8 indicated twice by single inscription.

In this way the number of leads of the driver board 38 and control unit connectors 43B and 43C can be reduced, this making managing the leads an easy matter.

The case side connector 48 is provided at the bottom end of the case side interrupt board 46. When the control box 19 is inserted in the case 20, the case side connector 48 is disposed at a position corresponding to the control box side connector 44 provided on the back side of the control box 19. Accordingly, the case side connector 48 engages the control box side connector 44 by inserting the control box 19 into the case 20. In this way power can be supplied and electric signals transferred from the control unit 18 to the previously described motors, sensors, liquid crystal display 40, and operation panel 41 through the control box side interrupt board 45 and case side interrupt board 46.

According to this configuration, an operator can expose the control unit 18 by pulling the control box 19 from the case 20 for easy inspection and maintenance, thus reducing the number of maintenance processes. Furthermore, since the connecting parts are connected between the control box 19 and case 20, the electrical connection is reliably cut off between the control unit 18 and the transport mechanism 16 when the control box 19 is pulled from the case 20, and therefore the operator can quickly perform her work by pulling out the control box 19. Furthermore, since there are only two control box side connectors 44 and case side connectors 48, the control box 19 is easily inserted into the case 20. A high degree of assembly precision is not necessary when assembling the sample rack transport apparatus 100.

Although there are two control box side connectors 44 and case side connectors 48, there may be any number of such connectors insofar as connector access is simple.

A driver circuit 57 provided on the case side interrupt board 46 is disposed near the actuator connector 47C. the driver circuit 57 is connected to the motor 51 through the actuator connector 47C. the driver circuit 57 is capable of driving the motor 51 based on motor control signals output from the CPU board 39. When a new motor is added, a new driver circuit 57 may be provided to the case side interrupt board 46.

In this way driver circuits can be provided to the case side interrupt board 46 when an additional new driver circuit 57 is required. Therefore, it is unnecessary to redesign the control unit 18, and the number of development processes, and cost can be reduced.

The driver board 38 is not necessarily required and the CPU board 39 may perform such duties insofar as power is supplied from a commercial power source and the installed power circuit is capable of converting the voltage of the commercial power to voltages that are usable by the sensors and CPU 39A. A new independent power circuit also may be provided within the control box 19.

Although motors are provided in the transport mechanism 16 in the present embodiment, the present invention is not limited to this arrangement inasmuch as other actuators, such as solenoids, air cylinders and the like.

An example of a sample rack transport system using the previously described sample rack transport apparatus 100 is illustrated below. FIG. 9 is a schematic view showing the general structure of the sample rack transport system, As shown in FIG. 9, a sample rack transport system 1 is provided with a transfer device 3, sample rack transport units 4 and 10 for transporting sample racks, two subsystems 1a, and data processing device 11 for displaying analysis results of a blood analyzer 9. The subsystems 1a mainly includes a rack transport unit 7 for transporting sample racks, rack destination change units 5 and 8 for receiving sample racks from any among a plurality of supply origins and delivering the received sample racks to any among a plurality of transport destinations, blood analyzer 9 for analyzing received samples, and sample rack transport apparatus 100 for supplying sample racks to the blood analyzer 9.

A tray is installed on the top surface of the transfer device 3. Sample racks 12 are placed in the tray. The transfer device 3 is provided with a receiving rack receiving unit 3a for placing sample racks 12 received from outside the apparatus onto the tray, rack feeding unit 3b for feeding the sample racks 12 on the tray to the rack transport unit 4, tray transport unit 3c for transporting the tray in the rightward direction, rack receiving unit 3d for receiving sample racks 12 received from the rack transport unit 10 onto the tray, and rack feeding unit 3e for sending the sample racks 12 on the tray to outside the apparatus. The rack receiving unit 3a, rack feeding unit 3b, tray transport unit 3c, rack receiving unit 3d, and rack feeding unit 3e are arranged sequentially from the left in a single row. The shapes of the rack receiving unit 3a, rack feeding unit 3b, tray transport unit 3c, rack receiving unit 3d, and rack feeding unit 3e are extended rectangles in the front-to-back direction.

The rack receiving unit 3a places sample racks 12 supplied from outside onto the tray in a line in the front-to-back direction. The tray with the lined up sample racks 12 is transported from the rack receiving unit 3a to the rack feeding unit 3b.

The rack feeding unit 3b is longer in the front-to-back direction than the rack receiving unit 3a, and projects toward the front farther than the front end of the rack receiving unit 3a. The right end of the rack transport unit 4 is connected to the left side surface of the front end of the rack feeding unit 3b. The rack feeding unit 3b transports the tray received from the rack receiving unit 3a forward, and supplies sample racks 12 arranged on the tray to the rack transport unit 4. After the sample racks 12 have been sent, the tray is returned in the back direction, and thereafter the sent to the tray transport unit 3c.

The tray transport unit 3c has a length in the front-to-back direction identical to that of the rack receiving unit 3a. The tray transport unit 3c transports the empty tray received from the rack feeding unit 3b to the rack receiving unit 3d.

The rack receiving unit 3d is even longer in the front-to-back direction than the rack feeding unit 3b, and the rack receiving unit 3d projects in the front direction beyond the front end of the rack feeding unit 3b. The right end of the rack transport unit 10 is connected to the left side surface of the front end of the rack receiving unit 3d. The rack receiving unit 3d transports trays received from the tray transport unit 3c in a forward direction. The sample racks 12 received from the rack transport unit 10 are placed on the tray arranged in a single row from front to back. After the sample racks 12 have been received, the tray is returned in the back direction, and thereafter, transported to the rack feeding unit 3e.

The rack feeding unit 3e supplies the sample racks 12 arranged on the received tray to the destination of the sample rack 12.

The rack transport unit 4 and rack transport unit 10 are arranged so as to be mutually parallel respectively narrow in the lateral direction. The left ends of the rack transport unit 4 and rack transport unit 10 are gripped and connected to the right side surface of the rack destination change unit 5. The transport units 4 and 10 have conveyor belts, and are configured so as to transport the sample racks 12 placed on the belt in a line by rotating the circular belts.

The structure of the subsystem 1a is described below. The subsystem 1a is provided with a sample rack transport apparatus 100, and a rack transport unit 7 is connected at the front side of the sample rack transport apparatus 100. A blood analyzer 9 is connected at the back side of the sample rack transport apparatus 100, a rack destination change unit 8 is connected at the left side of the sample rack transport apparatus 100, and a rack destination change unit 5 is connected at the right side of the sample rack transport apparatus 100.

Two subsystems 1a are linked laterally at the left side of the rack transport unit 4 and rack transport unit 10. A data processing apparatus 11 is disposed between the two blood analyzers 9, reach respectively having one subsystem 1a.

The rack destination change unit 5 has a belt line 5a. The belt line 5a transports the sample racks 12 in a lateral direction. The belt line 5a moves front-to-back. The front and back position of the belt line 5a and sample rack destination match, and the belt line 5a received the sample rack 12 by moving in a front-to-back direction. Thereafter, the destination of the sample rack 12 and front and back position of the belt line 5a match, and the sample rack 12 received by the belt line 5a is supplied to the destination by the belt line 5a moving front-to-back.

The positional relationship of the rack destination change unit 5 and the surrounding devices are described below individually since the rack destination change unit 5 provided on the right side and the rack destination change unit 5 provided on the left side are different.

In the rack destination change unit 5 provided on the right side, a rack transport unit 10 is connected to the center part of the surface on the right side, and a rack transport unit 4 is connected at the back end of the right side surface. A rack transport unit 7 described later is connected at the center part on the left side surface of the rack destination change unit 5, and a sample rack transport apparatus 100 is connected at the back end on the left side surface of the rack destination change unit 5. The rack destination change unit 5 moves the belt line 5a such that the belt line 5a matches the front-to-back position of either the belt line of the rack transport unit 4 or the belt line 7a described later, and receives the sample rack 12. The rack destination change unit 5 moves the belt line 5a such that the belt line 5a matches the front-to-back position of either the sample rack receiving part of the sample rack transport apparatus 100, a belt line 7b described later, or the belt line of the rack transport unit 10, so as to selectively supply the received sample rack 12 to either the sample rack transport unit 100, rack transport unit 7, or rack transport unit 10.

In the rack destination change unit 5 provided on the left side, a rack destination change unit 8 is connected on the right side surface. A rack transport unit 7 is connected at the center part on the left side surface of the rack destination change unit 5, and a sample rack transport apparatus 100 is connected at the back end on the left side surface. The rack destination change unit 5 moves the belt line 5a such that the belt line 5a matches the front-to-back position of either the belt line 8a described later or the belt line 7a, and receives the sample rack 12. The rack destination change unit 5 moves the belt line 5a such that the belt line 5a matches the front-to-back position of either the sample rack receiving part of the sample rack transport apparatus 100, a belt line 7b described later, or the belt line 8a, so as to selectively supply the received sample rack 12 to either the sample rack transport unit 100, rack transport unit 7, or rack destination change unit 8.

The rack transport unit 7 becomes narrow in the lateral direction, and has a belt line 7a for transporting the sample rack 12 to the right, and a belt line 7b for transporting the sample rack 12 to the left.

The blood analyzer 9 is connected to the back side of the sample rack transport apparatus 100. The blood analyzer (for example, a model XE-2100 made by Sysmex, Inc.) outputs the white cell count, red cell count, platelet count, and hemoglobin contained in the sample as basic measurement items, and further outputs reticulocyte count and five types of white blood cell data, including neutrophils, lymphocytes, monocytes, eosinophils, basophils.

The rack destination change unit 8 has a belt line 8a. Since the structure of the rack destination change unit 8 is identical to the structure of the rack destination change unit 5, further description is omitted.

The positional relationship of the rack destination change unit 8 and the surrounding devices are described below individually since the rack destination change unit 8 provided on the left side and the rack destination change unit 8 provided on the right side are different.

A rack transport unit 7 is connected at the center part on the right side surface of the rack destination change unit 8 provided on the left side, and a sample rack transport apparatus 100 is connected at the back end of the right side surface. Nothing is connected at the left side surface of the rack destination change unit 8. The rack destination change unit 8 moves the belt line 8a such that the belt line 8a matches the front-to-back position of either the sample rack feeding part of the sample rack transport apparatus 100, or a belt line 7b, and receives the sample rack 12. The rack destination change unit 8 moves the belt line 8a such that the belt line 8a matches the front-to-back position of the belt line 7a, and supplies the received sample rack 12 to the rack transport unit 7.

In the rack destination change unit 8 provided on the right side, a rack transport unit 7 is connected to the center part of the surface on the right side, and a rack transport apparatus 100 is connected at the back end on the right side. A rack destination change unit 5 is connected at the left side surface of the rack destination change unit 8. The rack destination change unit 8 moves the belt line 8a front-to-back, such that the belt line 8a matches the front-to-back position of either the sample rack feeding part of the sample rack transport apparatus 100, or a belt line 7b, and receives the sample rack 12. The rack destination change unit 8 moves the belt line 8a front-to-back such that the belt line 8a matches the front-to-back position of the belt line 5a, and selectively supplies the received sample rack 12 to the rack destination change unit 5 and rack transport unit 7.

The operation of the sample rack transport system 1 is described below when a sample is analyzed by the blood analyzer 9 provided on the right side.

Sample racks 12 received from outside are arranged in a single row front-to-back on a tray on top of the rack receiving unit 3a. The tray with the lined up sample racks 12 is transported to the right. Having reached the rack feeding unit 3b, the tray is transported forward and when the tray reaches the front end of the rack feed unit 3b, the sample racks 12 are supplied one by one to the rack transport unit 4. The rack transport unit 4 transports the received sample rack 12 to the left.

The rack destination change unit 5 moves the belt line 5a front-to-back to match the front-to-back position of the rack transport unit 4, and receives the sample rack 12 from the rack transport unit 4. The rack destination change unit 5 moves the belt line 5a front-to-back to match the front-to-back position of sample rack receiving part of the sample rack transport apparatus 100, so as to supply the received sample rack 12 to the sample rack transport unit 100.

The sample rack transport apparatus 100 stocks the sample rack 12 received from the rack destination change unit 5 in the start stocker 21, and transports the stocked sample racks 12 one by one to the sample supply position 22 (refer to FIG. 2) of the blood analyzer 9. The samples in the sample containers 14 are analyzed by the blood analyzer 9. Thereafter, the sample rack 12 is stocked in the previously described end stocker 23, and transported toward the rack destination change unit 8, which is connected to the sample rack transport apparatus 100.

The rack destination change unit 8 moves the belt line 8a front-to-back to match the front-to-back position of the sample rack feeding part of the sample rack transport apparatus 100, and receives the sample rack 12 from the sample rack transport apparatus 100. The rack destination change unit 8 moves the belt line 8a front-to-back to match the front-to-back position of the belt line 7a, and supplies the received sample rack 12 to the rack transport unit 7.

The belt line 7a transports the sample rack 12 received from the rack destination change unit 8 to the right. The rack destination change unit 5 receives the sample rack 12 from the rack transport unit 7, and supplies the received sample rack 12 to the rack transport unit 10.

The rack transport unit 10 transports the sample rack 12 received from the rack destination change unit 5 to the rack receiving unit 3d. The sample racks 12 are arranged in a single row front-to-back on the tray on the top of the rack receiving unit 3d. The tray with the lined up sample racks 12 is moved in the back direction, and transported the rack feed unit 3e on the right.

The embodiment disclosed above has been described by way of examples in all aspects and is not to be considered as restrictive in any sense. The scope of the present invention is defined solely by the appended claims, and is not affected to any degree by the statements within this summary. The present invention may be variously modified insofar as such modification is within the scope and equivalences of the claims.

What is claimed is:

1. A sample rack transport apparatus for transporting a sample rack holding a container containing a sample, comprising:
   a transport mechanism comprising:
   a first transporting member for transporting a rack in a first direction;
   a second transporting member for transporting the rack, transported by the first transporting member, in a second direction perpendicular to the first direction; and
   a third transporting member for transporting the rack, transported by the second transporting member, in a third direction opposite to the first direction;
   a control unit;
   a control box for housing the control unit;
   a case for accommodating the transport mechanism and the control box housing the control unit; and
   a guide member for guiding movement of the control box between a first position where the control box is accommodated in the case and a second position where the control box is withdrawn from the case;
   wherein the control unit housed in the control box is positioned below the transport mechanism when the control unit housed in the control box is positioned at the first position, and the control unit housed in the control box executes operations comprising:
   controlling the first transporting member so as to transport the rack placed on the case in the first direction;
   controlling the second transporting member so as to transport the rack, transported by the first transporting member, in the second direction; and
   controlling the third transporting member so as to transport the rack, transported by the second transporting member, in the third direction;
   where the first transporting member comprises a plurality of multi-actuating members which are actuated to selectively engage the rack and to move in a common direction for transporting the rack in the first direction and are retractile to the case.

2. The sample rack transport apparatus according to claim 1, wherein
   the transport mechanism has an actuator which is controlled by the control unit so as to transport the sample rack;
   the sample rack transport apparatus further comprises a case side connector connected to lead from the actuator;
   the control box further comprises a control box side connector which is connected to lead from the control unit and is connectable with the case side connector,
   wherein the control box side connector is arranged at the back end of the control box; and
   the control box side connector and case side connector are respectively arranged at positions so as to be mutually connectable when the control box is inserted into the apparatus so as to be guided by the guide member.

3. The sample rack transport apparatus according to claim 2, further comprising:
   an actuator side connector electrically connected to lead from the actuator; and
   a case side interrupt board having the case side connector and an actuator connector connected to lead from the case side connector;
   wherein the actuator connector is connectable to the actuator side connector and is disposed at a position near the corresponding actuator.

4. The sample rack transport apparatus according to claim 3, wherein the case side interrupt board has a driver circuit for driving the actuator based on electric signal from the control unit.

5. The sample rack transport apparatus according to claim 2, wherein the transport mechanism comprises a plurality of power receiving objects;
   the control unit further comprises a power supply for supplying power to the power receiving objects by power leads;
   the power leads connect the power supply with the power receiving objects through the control box side connector and the case side connector; and
   the power leads between the power supply and control box side connector are provided at a lesser number than the number of power receiving objects.

6. The sample rack transport apparatus according to claim 2, wherein the control box further comprises a control box side interrupt board having a control unit connector connected to leads from the control unit and the control box side connector connected to lead from the control unit connector.

7. The sample rack transport apparatus according to claim 1, wherein the control box comprises a projection member arranged on the side surfaces of the control box, and
   the guide member guides the control box by the connection of the guide member and the projection member.

8. The sample rack transport apparatus according to claim 1, wherein the control unit is configured by a plurality of boards.

9. The sample rack transport apparatus according to claim 1, further comprising a handle which is provided on the front end of the control box.

10. The sample rack transport apparatus according to claim 1, wherein the guide member comprises a guide rail.

11. The sample rack transport apparatus according to claim 1 further comprising a concave receiver with a depression on the top surface provided between the transport mechanism and the control box.

12. The sample rack transport apparatus according to claim 1, wherein
    the control box is comprised of a flat box provided with an opening at the top surface.

13. The sample rack transport apparatus according to claim 1, further comprising a panel member arranged between the transport mechanism and the control box in the case.

14. A sample rack transport apparatus for transporting a sample rack holding a container containing a sample that includes a transport mechanism comprising:
    a first transporting member for transporting a rack in a first linear direction;
    a second transporting member for transporting the rack, transported by the first transporting member, in a second linear direction substantially perpendicular to the first linear direction; and
    a third transporting member for transporting the rack, transported by the second transporting member, in a third linear direction opposite to the first linear direction;
    a control box enclosing a control unit;
    a case for accommodating the transporting mechanism and the control box; and
    a guide member for guiding movement of the control box between a first position where the control box is accommodated in the case and a second position where the control box is withdrawn from the case;

where the control box is positioned below the transport mechanism when the control unit enclosed in the control box is positioned at the first position, and the control unit executes operations comprising:

controlling the first transporting member so as to transport the rack placed on the case in the first linear direction;

controlling the second transporting member so as to transport the rack, transported by the first transporting member, in the second linear direction; and controlling the third transporting member so as to transport the rack, transported by the second transporting member, in the third linear direction where the first transport member comprises a plurality of multi-actuating members which are actuated to move in a common direction for transporting the rack in the first linear direction and the plurality of multi-actuating members engage the rack in a sliding engagement and are retractile to the case.

15. The sample rack transport apparatus according to claim 14 where the first transporting member, the second transporting member, and the third transporting member comprise movable linear members that move in different linear directions in a sequential order when actuated by the control unit.

16. The sample rack transport apparatus according to claim 15 where a proximal end of the second transporting member abuts the first transporting member and a distal end of the second transporting member abuts the third transporting member.

17. The sample rack transport apparatus according to claim 14 where the third transporting member comprises a second plurality of multi-actuating members which are actuated to move in a common direction for transporting the rack in separate directions and each of the plurality of multi-actuating members make contact with the rack in a sliding engagement.

* * * * *